(12) United States Patent
Koll et al.

(10) Patent No.: US 11,158,411 B2
(45) Date of Patent: Oct. 26, 2021

(54) COMPUTER-AUTOMATED SCRIBE TOOLS

(71) Applicant: MModal IP LLC, Franklin, TN (US)

(72) Inventors: Detlef Koll, Pittsburgh, PA (US);
Vasudevan Jagannathan, Morgantown, WV (US)

(73) Assignee: 3M INNOVATIVE PROPERTIES COMPANY, Saint Paul, MN (US)

(*) Notice: Subject to any disclaimer, the term of this patent is extended or adjusted under 35 U.S.C. 154(b) by 172 days.

(21) Appl. No.: 15/897,945

(22) Filed: Feb. 15, 2018

(65) Prior Publication Data

US 2018/0240538 A1 Aug. 23, 2018

Related U.S. Application Data

(60) Provisional application No. 62/460,791, filed on Feb. 18, 2017.

(51) Int. Cl.
*G16H 15/00* (2018.01)
*G10L 15/26* (2006.01)

(52) U.S. Cl.
CPC ............ *G16H 15/00* (2018.01); *G10L 15/26* (2013.01)

(58) Field of Classification Search
CPC ........ G16H 15/00; G10L 15/26; G10L 15/265
USPC ............................................................. 705/2
See application file for complete search history.

(56) References Cited

U.S. PATENT DOCUMENTS

| 6,304,848 | B1 | 10/2001 | Singer |
| 6,801,916 | B2 | 10/2004 | Roberge |
| 6,951,541 | B2 | 10/2005 | Desmarais |
| 7,016,844 | B2 | 3/2006 | Othmer |
| 7,031,998 | B2 | 4/2006 | Archbold |
| 7,272,575 | B2 | 9/2007 | Mae |
| 7,308,126 | B2 | 12/2007 | Rogers |
| 7,379,946 | B2 | 5/2008 | Carus |
| 7,418,123 | B2 | 8/2008 | Giger |
| 7,490,085 | B2 | 2/2009 | Walker |

(Continued)

FOREIGN PATENT DOCUMENTS

| CA | 2995696 A1 | 8/2018 |
| JP | 2009082441 | 4/2009 |

(Continued)

OTHER PUBLICATIONS

Zhao, Yunxin. "Speech-recognition technology in health care and special-needs assistance [Life Sciences]." IEEE Signal Processing Magazine 26.3 (2009): 87-90. (Year: 2009).*

(Continued)

*Primary Examiner* — Michael Tomaszewski
*Assistant Examiner* — Rachael Sojin Stone
(74) *Attorney, Agent, or Firm* — Blueshift IP LLC; Robert Plotkin (57) ABSTRACT

A computerized system processes the speech of a physician and a patient during a patient encounter to automatically produce a draft clinical report which documents the patient encounter. The draft clinical report includes information that has been abstracted from the speech of the physician and patient. The draft report is provided to the physician for review. Producing the draft clinical report automatically, rather than requiring the physician to prepare the draft clinical report manually, significantly reduces the time required by the physician to produce the final version of the clinical report.

20 Claims, 5 Drawing Sheets

(56) References Cited

U.S. PATENT DOCUMENTS

| | | | |
|---|---|---|---|
| 7,532,942 B2 | 5/2009 | Bruce | |
| 7,584,103 B2 | 9/2009 | Fritsch | |
| 7,599,534 B2 | 10/2009 | Krishnan | |
| 7,613,610 B1* | 11/2009 | Zimmerman | G06Q 50/22 704/235 |
| 7,716,040 B2 | 5/2010 | Koll | |
| 7,930,193 B2 | 4/2011 | Marx | |
| 7,933,782 B2 | 4/2011 | Bruce | |
| 7,937,277 B2 | 5/2011 | Marx | |
| 8,165,878 B2* | 4/2012 | Roberge | G10L 15/08 704/243 |
| 8,312,057 B2 | 11/2012 | Chowalloor | |
| 8,335,689 B2 | 12/2012 | Wittenstein | |
| 8,412,522 B2 | 4/2013 | Boes | |
| 8,700,694 B2 | 4/2014 | Archbold | |
| 8,781,829 B2 | 7/2014 | Koll | |
| 8,856,188 B2 | 10/2014 | Reiner | |
| 8,903,901 B2 | 12/2014 | Archbold | |
| 8,930,178 B2 | 1/2015 | Pestian | |
| 9,240,185 B2 | 1/2016 | Boes | |
| 9,477,809 B2 | 10/2016 | Marx | |
| 9,513,355 B2* | 12/2016 | Ritter | G01R 33/3607 |
| 9,569,594 B2* | 2/2017 | Casella dos Santos | G16H 40/63 |
| 9,704,111 B1 | 7/2017 | Antunes | |
| 9,761,226 B2 | 9/2017 | Michaelangelo | |
| 10,339,937 B2 | 7/2019 | Koll et al. | |
| 2003/0120517 A1 | 6/2003 | Eida | |
| 2004/0120557 A1 | 6/2004 | Sabol | |
| 2005/0187802 A1 | 8/2005 | Koeppel | |
| 2006/0106641 A1 | 5/2006 | Bartsch et al. | |
| 2006/0241943 A1 | 10/2006 | Benja-Athon | |
| 2006/0274928 A1* | 12/2006 | Collins | A61B 6/00 382/132 |
| 2007/0038499 A1 | 2/2007 | Margulies et al. | |
| 2007/0288268 A1 | 12/2007 | Week | |
| 2009/0089100 A1 | 4/2009 | Nenov | |
| 2009/0106047 A1 | 4/2009 | Bay | |
| 2009/0132254 A1 | 5/2009 | Fitzgerald | |
| 2010/0063845 A1* | 3/2010 | Yeluri | G06Q 50/22 705/3 |
| 2010/0094656 A1 | 4/2010 | Conant | |
| 2010/0135562 A1 | 6/2010 | Greenberg | |
| 2010/0145720 A1 | 6/2010 | Reiner | |
| 2011/0054933 A1 | 3/2011 | Johnson | |
| 2011/0282687 A1* | 11/2011 | Koll | G06Q 10/10 705/3 |
| 2012/0029963 A1 | 2/2012 | Olding | |
| 2012/0173281 A1 | 7/2012 | Dilella | |
| 2012/0215551 A1 | 8/2012 | Flanagan | |
| 2012/0221347 A1 | 8/2012 | Reiner | |
| 2012/0239429 A1 | 9/2012 | Corfield | |
| 2012/0290299 A1* | 11/2012 | Basson | G06F 40/30 704/235 |
| 2012/0323574 A1 | 12/2012 | Wang et al. | |
| 2013/0051545 A1 | 2/2013 | Ross et al. | |
| 2013/0238329 A1 | 9/2013 | Casella Dos Santos | |
| 2013/0238330 A1 | 9/2013 | Casella dos Santos | |
| 2013/0311190 A1 | 11/2013 | Reiner | |
| 2013/0317871 A1 | 11/2013 | Kulkarni | |
| 2014/0019128 A1 | 1/2014 | Riskin | |
| 2014/0037162 A1 | 2/2014 | Papier | |
| 2014/0046185 A1* | 2/2014 | Mo | A61B 8/461 600/443 |
| 2014/0222462 A1 | 8/2014 | Shakil | |
| 2014/0298409 A1 | 10/2014 | Mock et al. | |
| 2014/0316772 A1 | 10/2014 | Koll et al. | |
| 2014/0363074 A1* | 12/2014 | Dolfing | G06K 9/6821 382/156 |
| 2014/0365232 A1 | 12/2014 | Sadeghi | |
| 2015/0066529 A1 | 3/2015 | Lattuca et al. | |
| 2015/0254596 A1 | 9/2015 | Nayar et al. | |
| 2016/0132815 A1 | 5/2016 | Itoko et al. | |
| 2016/0147954 A1 | 5/2016 | Babaji | |
| 2016/0155227 A1* | 6/2016 | Chae | A61B 8/4254 382/131 |
| 2016/0170975 A1* | 6/2016 | Jephcott | G06Q 10/10 704/3 |
| 2016/0171708 A1* | 6/2016 | Kim | G06T 7/11 382/128 |
| 2016/0336023 A1 | 11/2016 | Guyott et al. | |
| 2016/0350497 A1 | 12/2016 | Sharbell | |
| 2016/0361025 A1 | 12/2016 | Reicher | |
| 2016/0364528 A1 | 12/2016 | Reicher | |
| 2016/0364631 A1 | 12/2016 | Reicher | |
| 2017/0147763 A1 | 5/2017 | Marx | |
| 2017/0169191 A1* | 6/2017 | Bowers | G16H 10/20 |
| 2018/0232259 A1 | 8/2018 | Chowdhury et al. | |
| 2018/0240061 A1 | 8/2018 | Gransden | |
| 2018/0373844 A1 | 12/2018 | Ferrandez-Escamez et al. | |
| 2018/0376002 A1 | 12/2018 | Abraham | |
| 2019/0272921 A1 | 9/2019 | Koll | |

FOREIGN PATENT DOCUMENTS

| | | | |
|---|---|---|---|
| JP | 2012143368 A | | 8/2012 |
| JP | 2015035099 A | * | 2/2015 |
| WO | 2018031919 A1 | | 2/2018 |
| WO | 2018152352 | | 8/2018 |
| WO | 2019169242 A1 | | 9/2019 |

OTHER PUBLICATIONS

International Search Report and Written Opinion received for International Patent Application No. PCT/US2019/020245, dated Jun. 14, 2019, 10 pages.

International Preliminary Report on Patentability, dated Aug. 29, 2019, in international patent application No. PCT/US2018/018406, 9 pages.

Gary C. David et al., "Listening to what is said—transcribing what is heard: the impact of speech recognition technology (SRT) on the practice of medical transcription (MT)," Sociology of Health & Illness, vol. 31, Issue 6, Sep. 2009, pp. 924-938.

Jeffrey Klann et al., "An Intelligent Listening Framework for Capturing Encounter Notes from a Doctor-Patient Dialog," BMC Med Inform Decis Mak. 2009; 9(Suppl 1): S3, Published online Nov. 3, 2009. doi: 10.1186/1472-6947-9-S1-S3, 5 pages.

Microsoft "EmpowerMD—Medical Conversations to Medical Intelligence" Feb. 20, 2018, Video available online at: https://www.microsoft.com/en-us/research/project/empowermd/ Accessed on Mar. 9, 2018 [transcription of video 1 page].

Non-Final Rejection dated Feb. 4, 2020 for U.S. Appl. No. 15/899,447 of Ian Gransden, filed Feb. 20, 2018, 47 pages.

Extended European Search Report dated Nov. 9, 2020, in European patent application No. 18754553.8, 9 pages.

Houston, J.D., & Rupp, F.W., "Experience with implementation of a radiology speech recognition system", Journal of digital imaging, vol. 13, No. 3, pp. 124-128. https://doi.org/10.1007/BF03. (Year: 2000).

Non-Final Rejection dated Sep. 16, 2020 for U.S. Appl. No. 16/290,042 of Detlef Koll, filed Jan. 3, 2019, 62 pages.

* cited by examiner

COMPUTER-AUTOMATED SCRIBE TOOLS

CROSS REFERENCE TO RELATED APPLICATIONS

This application claims priority from U.S. Provisional Patent Application Ser. No. 62/460,791, filed on Feb. 18, 2017, entitled "Computer-Automated Scribe Tools," which is hereby incorporated by reference.

BACKGROUND

When a physician or other healthcare professional provides healthcare services to a patient or otherwise engages with a patient in a patient encounter, the healthcare professional typically creates documentation of that encounter in a separate work step at some point after the patient encounter has concluded, such as immediately after the patient encounter or at the end of the work day. Creating such documentation can be tedious, time consuming, prone to error, and otherwise burdensome to the healthcare professional, even if the healthcare professional creates the documentation by dictating the documentation rather than writing it by hand or typing it.

SUMMARY

A computerized system processes the speech of a physician and a patient during a patient encounter to automatically produce a draft clinical report which documents the patient encounter. The draft clinical report includes information that has been abstracted from the speech of the physician and patient. The draft report is provided to a scribe or to the physician for review. Producing the draft clinical report automatically, rather than requiring the physician to prepare the draft clinical report manually, significantly reduces the time required by the physician to produce the final version of the clinical report.

Other features and advantages of various aspects and embodiments of the present invention will become apparent from the following description and from the claims.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

As described above, when a physician or other healthcare professional provides healthcare services to a patient or otherwise engages with a patient in a patient encounter, the healthcare professional typically creates documentation of that encounter in a separate work step at some point after the patient encounter has concluded, such as immediately after the patient encounter or at the end of the work day. More specifically, a typical workflow of many physicians when treating patients is the following:
  (1) Prepare for the patient visit by reviewing information about the patient in an Electronic Medical Record (EMR) system.
  (2) Engage in the patient encounter, such as by:
    a. Meeting with the patient in a treatment room.
    b. Discussing, with the patient, the reason for the visit, any changes in the patient's health conditions, medications, etc.
    c. Examining the patient.
    d. Discussing the physician's findings and plan with the patient.
    e. Entering any required follow up actions and medication orders into the EMR.
  (3) Create a clinical report of the patient encounter, containing information such as the care provided to the patient and the physician's treatment plan, such as by any one or more of the following:
    a. Writing or speaking a free form text narrative, beginning with a blank editing screen. If the physician speaks, the physician's speech may be transcribed verbatim into the editing screen using automatic speech recognition (ASR) software.
    b. Starting with a document template containing partial content, such as section headings and partially completed sentences, and filling in the missing information from the patient encounter, whether by typing or speaking.
    c. Using a structured data entry user interface to enter discrete data elements and free form text, such as by selecting discrete data elements using buttons and drop-down lists, and typing or speaking free form text into text fields.
    d. Dictation transcription just into a microphone—not necessarily in front of a screen as in (3) a.

The resulting clinical report may contain higher order reasoning and summarization of the patient encounter, which may go beyond the information that would otherwise be contained in a literal transcript of the dialog that occurred between the physician and patient in the patient encounter (referred to herein as the "care dialog"). Much of the information that is contained in the clinical report, however, is contained explicitly in the care dialog, and could be abstracted from the care dialog by a trained operator who does not have deep clinical qualifications. This process of abstracting information from the care dialog into the clinical report may not, however, result in either a literal transcript of the care dialog or a traditional summary of the content of the care dialog. Instead, the result of such abstraction may be content in the clinical report which constitutes a formalized description of the salient key facts that were touched upon in the care dialog.

For example, if the following text were contained in a literal transcript of the care dialog, such text may be omitted from the clinical report by the abstraction process described above, because such text is non-contributory (i.e., not relevant to or required by the clinical report):

Patient: I'm a little concerned because in a couple weeks I have a wedding and I need to be ready by then.
Dr.: Who's getting married.
Patient: My daughter.
Dr.: Oh, congratulations.
Patient: Thank you, thank you.
Dr.: You seem young to have a daughter who's getting married.
Patient: I do, I do, but yes.

The above example, in which all of the text above may be omitted entirely by the clinical report, illustrates the difference between the abstraction process described herein and a summarization process, which might include a summary of the text above, even though it is not relevant to the clinical report.

The abstraction process described herein may, however, summarize certain information in the care dialog if that information is relevant to the requirements of the clinical report but not necessary to include in its entirety in the clinical report. For example, consider the following portion of a care dialog:

Dr.: Um, so have you had a fever at all?
Patient: I don't think so. Sometimes I feel probably a little bit above my regular temperature, but I haven't had things like chills or . . .
Dr.: Ok, so no chills, are you taking your temperature at home?
Patient: Uh, no I didn't, but I have felt a little tired . . . .
Dr.: OK.

The abstraction process described herein may summarize the portion of the care dialog above as, for example, "Denies fevers, chills. Does not check temperatures. Feels fatigued."

In general, embodiments of the present invention include computerized systems and methods which record and process a care dialog to automatically generate those portions of a clinical report which can be generated automatically based on the care dialog, thereby reducing the amount of time required by the physician to create the clinical report.

Figure 1:
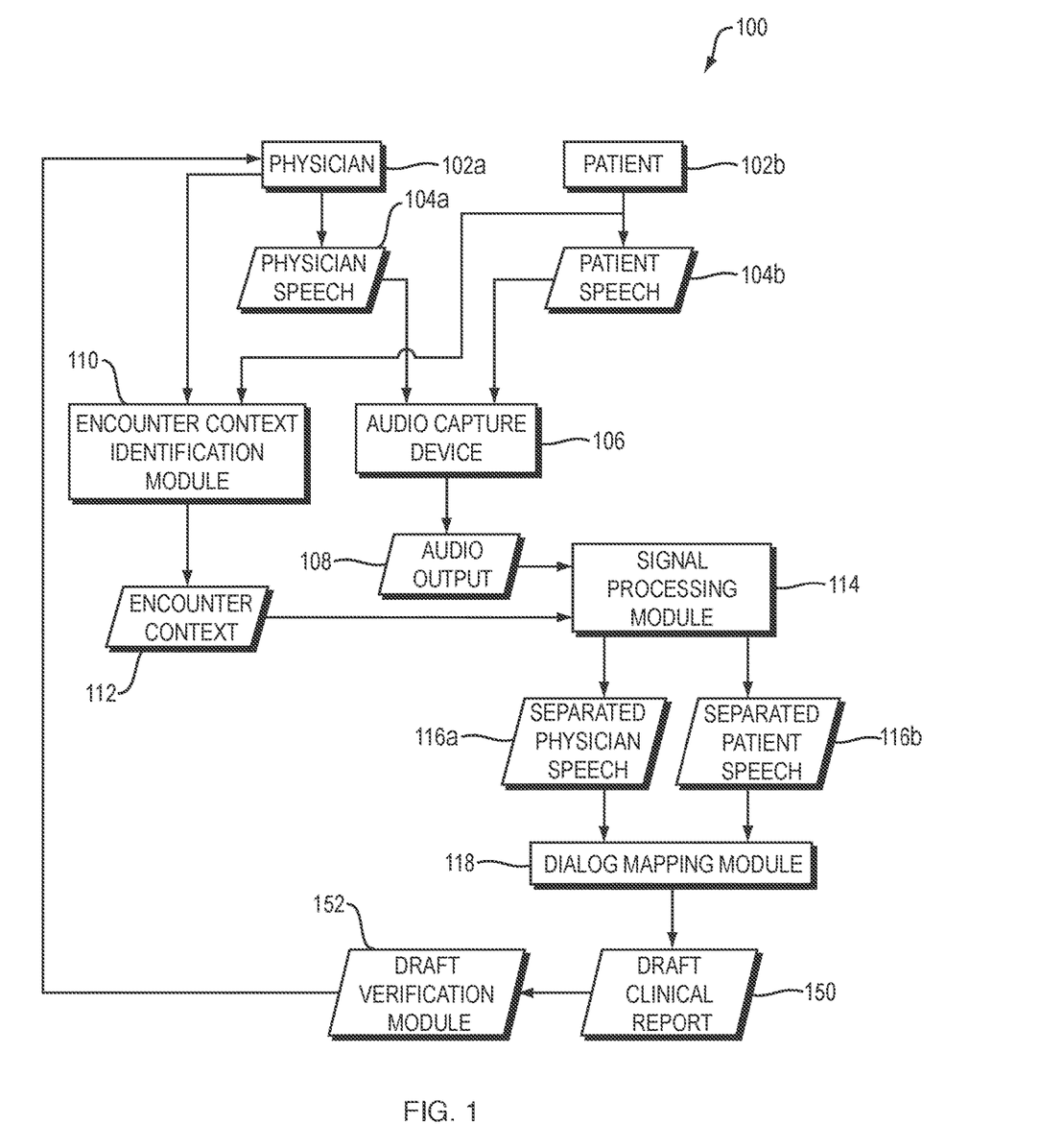
FIG. 1 is a dataflow diagram of a system for automatically generating a clinical report of an encounter between a physician and a patient according to one embodiment of the present invention.
Figure 2A:
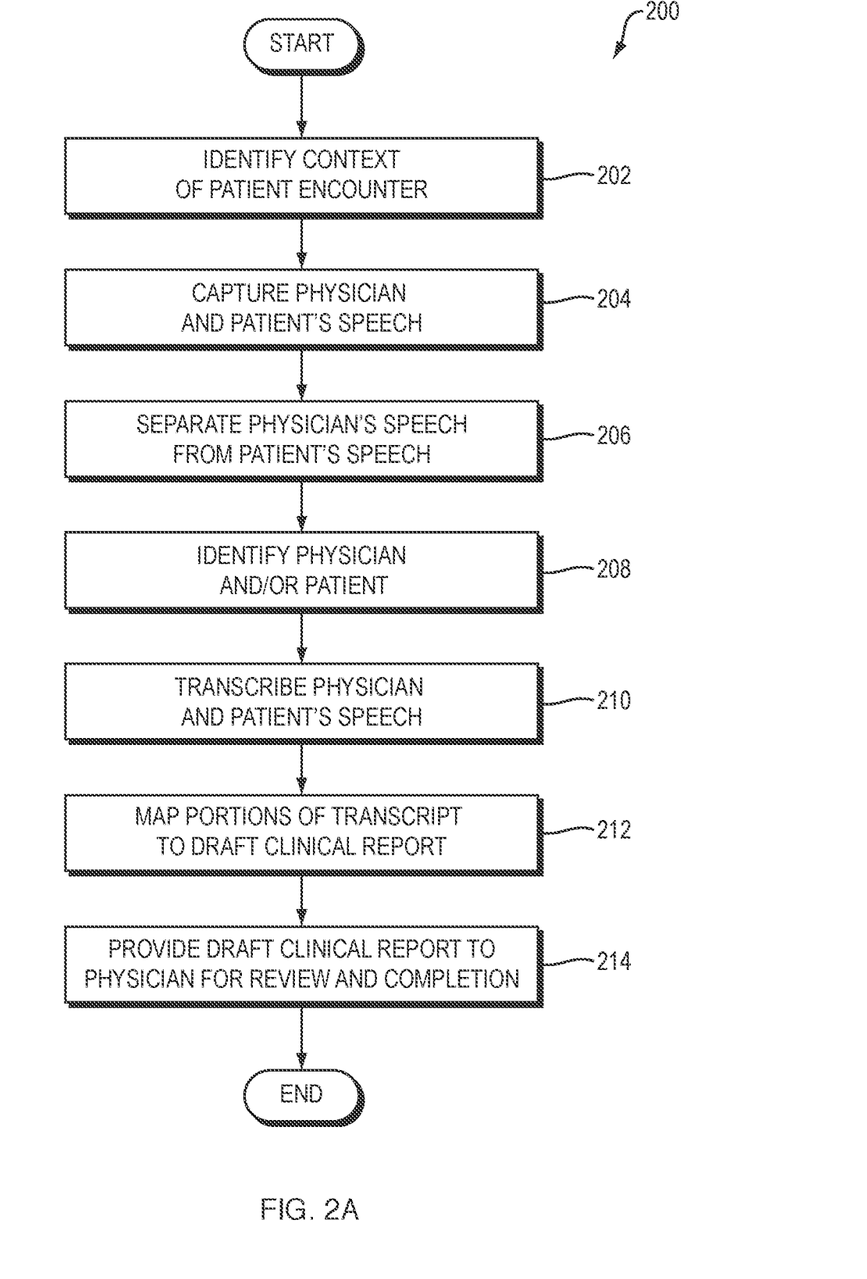
FIG. 2A is a flowchart of a method performed by the system of FIG. 1 according to one embodiment of the present invention.

More specifically, referring to FIG. 1, a dataflow diagram is shown of a system 100 for automatically generating a clinical report 150 of an encounter between a physician 102a and a patient 102b according to one embodiment of the present invention. Referring to FIG. 2, a flowchart is shown of a method 200 performed by the system 100 of FIG. 1 according to one embodiment of the present invention.

The system 100 includes a physician 102a and a patient 102b. More generally, the system 100 may include any two or more people. For example, the role played by the physician 102a in the system 100 may be played by any one or more people, such as one or more physicians, nurses, radiologists, or other healthcare providers, although embodiments of the present invention are not limited to use in connection with healthcare providers. Similarly, the role played by the patient 102b in the system 100 may be played by any one or more people, such as one or more patients and/or family members, although embodiments of the present invention are not limited to use in connection with patients. The physician 102a and patient 102b may, but need not, be in the same room as each other or otherwise in physical proximity to each other. The physician 102a and patient 102b may instead, for example, be located remotely from each other (e.g., in different rooms, buildings, cities, or countries) and communicate with each other by telephone/videoconference and/or over the Internet or other network.

The system 100 also includes an encounter context identification module 110, which identifies and/or generates encounter context data 112 representing properties of the physician-patient encounter (FIG. 2, operation 202). The encounter context identification module 110 may, for example, generate the encounter context data 112 based on information received from the physician 102a and/or the patient 102b or an EMR. For example, the physician 102a may explicitly provide input representing the identity of the physician 102a and/or patient 102b to the encounter context identification module 110. The encounter context identification module 110 may generate the encounter context data 112 using speaker identification/verification techniques. As an example of speaker verification techniques, a user may provide credentials to a log-in user interface (not shown), which the system 100 uses to identify the speaker; the system 100 may also optionally verify that the speaker is authorized to access the system 100. As another example, the user may provide credentials via a speech-based speaker verification system. As another example, the patient 102b may explicitly provide input representing the identity of the physician 102a and/or patient 102b to the encounter context identification module 110. As another example, the encounter context identification module 110 may identify the patient 102b based on data from another system, such as an EMR or a scheduling system which indicates that the patient 102b is scheduled to see the physician 102a at the current time.

Regardless of how the encounter context identification module 110 generates the encounter context data 112, the encounter context data 112 may, for example, include data representing any one or more of the following, in any combination:

Patient context data representing information about the patient 102b that is known before the patient encounter, such as any one or more of the following, in any combination:
The identity of the patient 102b.
Demographic information about the patient 102b, such as gender and age.
Medical information about the patient 102b, such as known past or current problems, especially major health problems (e.g., cancer) or chronic conditions, current and past medications, allergies, and recent lab values.

Physician context data representing information about the physician 102a, such as any one or more of the following, in any combination:
The identity of the physician 102a.
The medical specialty and setting of care of the physician 102a.
Explicit preferences of the physician 102a, such as document templates to be used, macro expansions (e.g., identifying a preference for expressing routine findings, such as ".nfc" that should be expanded to "No fever or chills"), rules for documenting specific procedures, and typing guidelines (e.g., which terms to abbreviate and which terms to spell out fully).
Implicit preferences of the physician 102a, which may be derived automatically by the system 100 based on previous clinical reports associated with the physician 102a, such as verbosity and word choice of the physician 102a.

Patient encounter context, such as the reason for the visit, e.g., the patient 102b's chief complaint, the location of the encounter, and the type of the encounter (e.g., well visit, follow up after a procedure, scheduled visit to monitor a chronic condition).

Work in progress data, such as any one or more of the following, in any combination:

A partially clinical report 150 for the patient encounter, including the text of the note, the current cursor position in the note, and the left and right textual context of the cursor in the note.

The output of a natural language understanding subsystem for classifying and/or encoding the semantic content of the partially generated clinical report 150 as it is being typed.

The output of a dialog processing system (e.g., system 100).

Now assume that the physician 102a and patient 102b speak during the physician 102a's encounter with the patient 102b. The physician's speech 104a and patient's speech 104b are shown as elements of the system 100. The physician 102a's speech 104a may, but need not be, directed at the patient 102b. Conversely, the patient 102b's speech 104b may, but need not be, directed at the physician 102a. The system 100 includes an audio capture device 106, which captures the physician's speech 104a and the patient's speech 104b, thereby producing audio output 108 (FIG. 2, operation 204). The audio capture device 106 may, for example, be one or more microphones, such as a microphone located in the same room as the physician 102a and the patient 102b, or distinct microphones spoken into by the physician 102a and the patient 102b. In the case of multiple audio capture devices, the audio output may include multiple audio outputs, which are shown as the single audio output 108 in FIG. 1 for ease of illustration.

The audio output 108 may, for example, contain only audio associated with the patient encounter. This may be accomplished by, for example, the audio capture device 106 beginning to capture the physician and patient speech 104a-b at the beginning of the patient encounter and terminating the capture of the physician and patient speech 104a-b at the end of the patient encounter. The audio capture device 106 may identify the beginning and end of the patient encounter in any of a variety of ways, such as in response to explicit input from the physician 102a indicating the beginning and end of the patient encounter (such as by pressing a "start" button at the beginning of the patient encounter and an "end" button at the end of the patient encounter). Even if the audio output 108 contains audio that is not part of the patient encounter, the system 100 may crop the audio output 108 to include only audio that was part of the patient encounter.

The system 100 may also include a signal processing module 114, which may receive the audio output 108 as input, and separate the audio output 108 into separate audio signals 116a and 116b representing the physician speech 104a of the physician 102a and the patient speech 104b of the patient 102b, respectively (FIG. 2, operation 206). The signal processing module 114 may use any of a variety of signal source separation techniques to produce the separated physician speech 116a and the separated patient speech 116b, which may or may not be identical to the original physician speech 104a and patient speech 104b, respectively. Instead, the separated physician speech 116a may be an estimate of the physician speech 104a and the separated patient speech 116b may be an estimate of the patient speech 104b.

The separated physician speech 116a and separated patient speech 116b may contain more than just audio signals representing speech. For example, the signal processing module 114 may identify the physician 102a (e.g., based on the audio output 108 and/or the encounter context data 112) and may include data representing the identity of the physician 102a in the separated physician speech 116a.

Similarly, the signal processing module 114 may identify the patient 102b (e.g., based on the audio output 108 and/or the encounter context data 112) and may include data representing the identity of the patient 102b in the separated patient speech 116b (FIG. 2, operation 208). The signal processing module 114 may use any of a variety of speaker clustering, speaker identification, and speaker role detection techniques to identify the physician 102a and patient 102b and their respective roles (e.g., physician, nurse, patient, parent, caretaker).

As another example, the signal processing module 114 may apply conversational speech recognition to the audio output 108 to produce a literal or non-literal (e.g., approximate) transcript of the audio output 108 (FIG. 2, operation 210). The signal processing module 114 may also take the encounter context data 112 (e.g., the identity of the physician 102a and/or patient 102b) into account when producing the transcript of the audio output 108. The signal processing module 114 may include the transcript in the separated physician speech 116a, the separated patient speech 116b, or in separate output (not shown).

Figure 3:
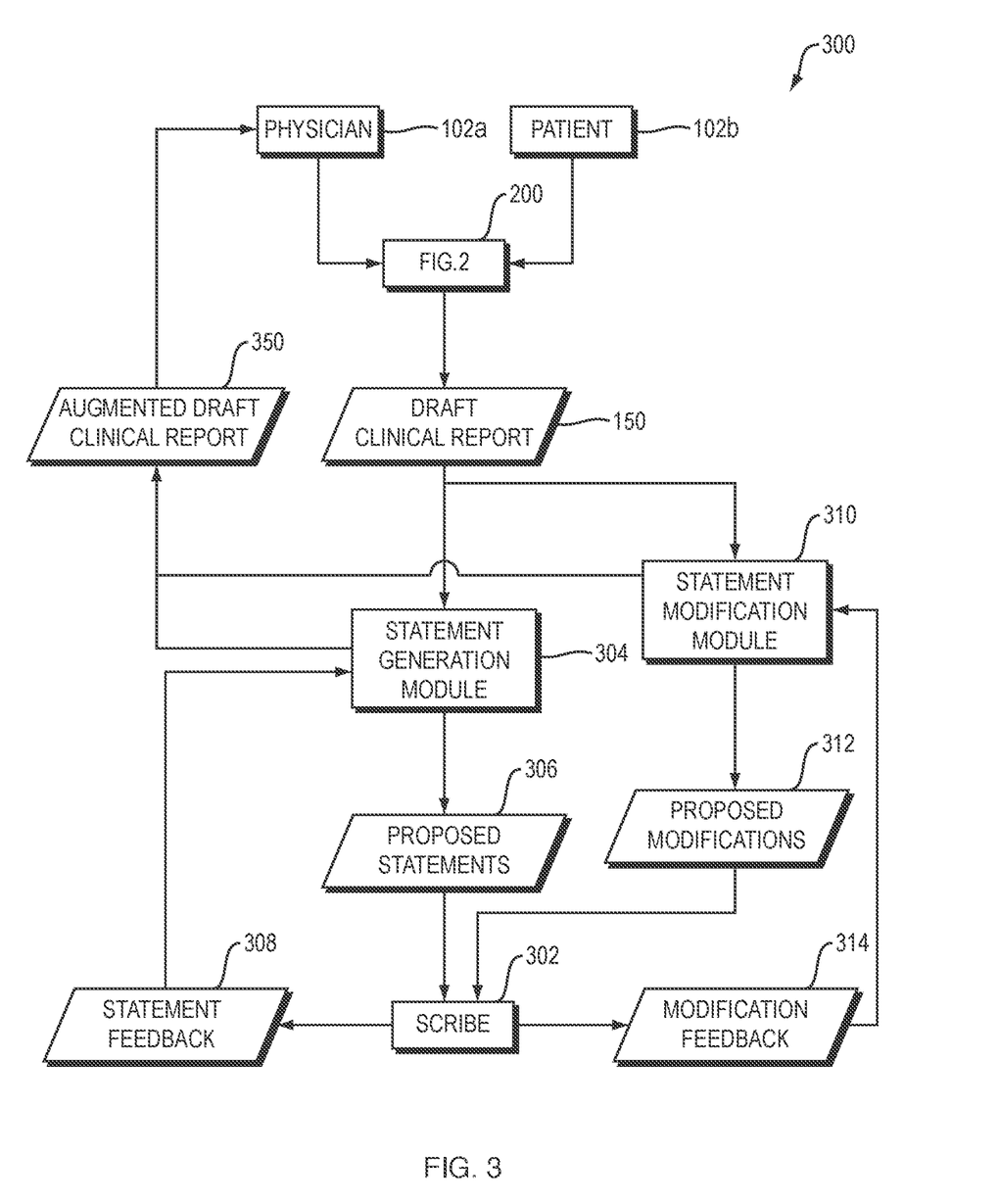
FIG. 3 is a dataflow diagram of a system for automatically generating an augmented draft clinical report of an encounter between the physician and a patient according to one embodiment of the present invention.

The system 100 also includes a dialog mapping module 118 (which may be integrated with the signal processing module 114), which maps segments of the physician and patient speech 116a and 116b to appropriate representations in the clinical report 150 (FIG. 2, operation 212). In some embodiments, a statement generation module 304 and a statement modification module 310, described in detail below in connection with FIG. 3, provide the functionality of the dialog mapping module 118. Examples of such appropriate representations include:

adding free form narrative in the speech 116a-b to the appropriate corresponding section in the clinical report 150 (e.g., adding text describing the patient 102'b current medications to a "Current Medications" section of the clinical report 150); and making an entry in a structured form of an EMR system based on a portion of the speech 116a-b (e.g., checking check box or selecting a number from a dropdown list).

The system 100 may also include a draft verification module 152, which may provide the clinical report 150 to the physician 102a (or to a scribe) for review, verification, and completion (FIG. 2, operation 214). The physician 102a (or scribe) may then review the report and edit it as desired before submitting it as a complete clinical report.

In addition to the functions performed above, the system 100 (e.g., the signal processing module 114 and/or the dialog mapping module 118) may identify the type of the patient encounter based on any one or more of the following, in any combination: the encounter context data 112, the audio output 108, the separated physician speech 116a, the separated patient speech 116b, information retrieved from an EMR system, and information retrieved from a scheduling system. The system 100 may, for example, identify the type of the patient encounter based on speech of the physician 102a or patient 102b which describes the patient encounter as being of a particular type. The system 100 may update the encounter context data 112 with the identified type of patient encounter.

The system 100 may put information contained in the care dialog (e.g., the speech 104a-b and/or 116a-b) in context with information about the patient 102b, contained in an EMR system. The system 100 may, for example, store data representing associations between data about the patient in the EMR system and portions of the speech 104a-b and/or 116a-b.

The system 100 may also personalize the content of the draft clinical report 150 to reflect the style and/or preferences of the dictating physician 102a, such as style and/or preferences relating to word choice, the type of information to include in the clinical report 150, and the amount of detail to include in the clinical report 150.

Embodiments of the present invention have a variety of advantages. For example, as described above, healthcare professionals (such as the physician 102a in FIG. 1) typically create documentation of their encounters with patients (such as the patient 102b in FIG. 1) in a separate work step after the encounter has concluded, and doing so is burdensome. Embodiments of the present invention address this problem by using computer-automated technology to substantially reduce the amount of time and effort required by the healthcare professional to document the patient encounter. In particular, embodiments of the present invention do this by automatically "listening" to the physician-patient dialog that occurs naturally during the patient encounter, whether in real-time (i.e., while the patient encounter is occurring), or afterwards, by processing a recording of the physician-patient dialog. Because embodiments of the present invention produce draft clinical reports based on the natural dialog that occurs between physician and patient, neither the physician nor the patient need to tailor their speech to the needs of the system nor take extra time to speak to or otherwise provide separate input to the system.

Furthermore, as described above, the clinical report 150 may be a structured document or otherwise have a particular predetermined structure, such as a predetermined set of sections organized in a particular sequence. Embodiments of the present invention may automatically map content (e.g., transcribed speech of the physician 102a and/or patient 102b) into the appropriate corresponding structures (e.g., sections) in the clinical report 150. This may result in content being inserted into the clinical report 150 in a different sequence than that in which the content was spoken by the physician 102a or patient 102b. For example, the clinical report 150 may contain a "Findings Section" followed by a "Diagnosis" section, while the physician 102a may first speak about the physician's diagnosis and then speak about the physician's findings. By inserting content into the clinical report 150 in the sequence required by the structure of the clinical report 150, which may not be the same as the sequence in which the content was dictated, embodiments of the present invention may be used to create a clinical report which is easier to review and revise, and which complies with applicable conventions and standards, regardless of the sequence of the topics covered by the physician and patient's speech 104a-b; a computing device executing a document generation system such as the system 100 that may generate new content and insert the content into a document in a sequence other than the dictation sequence results in an improved computing device providing non-conventional, non-generic functionality.

Similarly, and as described above, embodiments of the present invention may omit, from the clinical report 150, dictated content that is not relevant to the clinical report 150, where relevance may be determined, for example, based on the structure of the clinical report 150. For example, if the dialog mapping module 118 determines (e.g., through the implementation of natural language processing of speech 116a-b) that a portion of the speech 116a-b refers to the patient 102b's holiday plans, and the dialog mapping module 118 does not identify any section in the clinical report 150 that relates to holiday plans, then the dialog mapping module 118 may conclude that the portion of the speech 116a-b that refers to holiday plans is not relevant to the clinical report 150 and may, in response to this conclusion, omit that portion of the speech 116a-b and any corresponding transcribed text from the clinical report 150. In this way, embodiments of the present invention may omit irrelevant information from the clinical report 150 and thereby make the clinical report 150 easier to review and revise.

In the healthcare industry, a person known as a "scribe" often is employed to listen to the speech 104a-b of the physician 102a and patient 102b during the patient encounter. Often the scribe is physically present in the room with the physician 102a and patient 102b, and uses a laptop or tablet computer to type notes as the physician 102a and patient 102b speak to each other. Sometimes, however, the scribe is located remotely from the physician 102a and patient 102b, and listens to the physician-patient care dialog over an Internet connection.

Embodiments of the present invention may be used to help such a scribe to prepare the draft clinical report 150 so that the draft clinical report 150 is compliant with regulations and reflects complete information from the patient encounter. Such drafts may be presented in a "scratch pad" like structure to facilitate review and incorporation into the EMR by copy/paste or drag and drop methods. As one example of such facilitation, functionality provided in connection with a scratch pad area of a user interface may be used to alert a physician or scribe about various aspects related to clinical documentation, including creating reminders and automatically removing reminders once the draft clinical report 150 addresses a modification or requirement specified by the reminder. Furthermore, embodiments of the present invention may automatically create the draft clinical report 150 to be written in the personal style of the physician 102a who treated the patient 102b in the patient encounter.

Figure 2B:
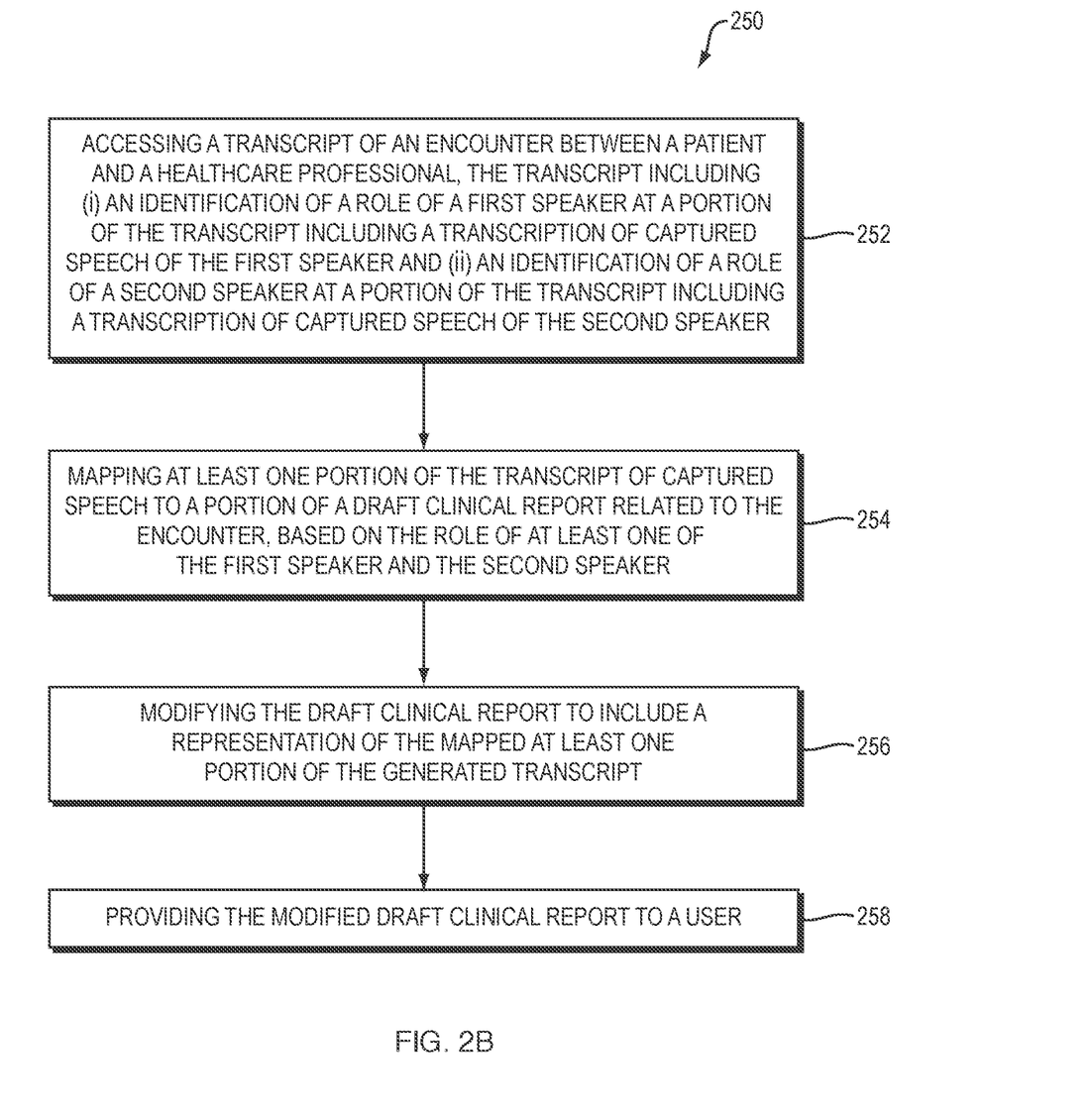
FIG. 2B is a flowchart of a method performed by the system of FIG. 1 according to another embodiment of the present invention.

The method described in connection with FIG. 2A describes an embodiment in which the system 100 captures physician's and patient's speech, separates the speech of the physician and the patient, and transcribes the speech of both speakers. However, in some embodiments, and as shown in FIG. 2B, the system 100 executes a method 250 for automatically modifying a draft clinical report to incorporate representations of data generated based on data extracted from captured speech and does so by accessing a transcript generated independently of the system 100. In such an alternative embodiment, the method 250 depicted in FIG. 2B includes accessing a transcript of an encounter between a patient and a healthcare professional, the transcript including (i) an identification of a role of a first speaker at a portion of the transcript including a transcription of captured speech of the first speaker and (ii) an identification of a role of a second speaker at a portion of the transcript including a transcription of captured speech of the second speaker (252). The method 250 may include receiving an identification of the first speaker (e.g., the patient, the physician, or other healthcare provider or person present during a healthcare encounter).

The method 250 includes mapping at least one portion of the transcript of captured speech to a portion of a draft clinical report related to the encounter, based on the role of at least one of the first speaker and the second speaker (254). Roles may be, for example, patient, physician, scribe, health care provider, caretaker, family member, or any other identifier of a speaker's role in a healthcare encounter. The mapping may also, or alternatively, be completed based on an identification of one of the first speaker and the second speaker (e.g., Dr. Martinez or Patient Smith). The mapping may also, or alternatively, be completed based on any content available within the transcript of the captured speech.

As will be described in greater detail below in connection with FIG. 3, the system may leverage machine translation and/or natural language processing to map a portion of the transcript. For example, a statement made by one of the speakers in the encounter may be mapped to a representative form by applying machine learning techniques to a statement (such as "you really should stop smoking") to identify keywords or concepts (e.g., "stop smoking" or "smoking cessation") and use those keywords or concepts to identify, in a data structure, a statement mapped to the keywords or concepts or mapped directly to the text of one or more statements as transcribed (e.g., "stop smoking" may be mapped to "I recommended to the patient to stop smoking"). The system may also generate text from discrete coding of information; for example, the system may extract observations from the transcript of captured speech for use in modifying, or proposing a modification to, a "review of systems" section of the draft clinical report 150; for example, the system may identify an observation such as a blood pressure result, a pulse, a weight, a lung examination observation or other observation and determine that a data structure maps the observation to a narrative for use in the draft clinical report 150. The system may also implement natural language generation techniques to generate text representative of information in the transcript, for insertion into the draft clinical report 150.

Additionally, the system may use data stored in the patient encounter context in connection with sentiment analysis techniques, semantic analysis techniques, and other techniques for identifying meta observations within a transcript; the system may then use the meta observations to identify a modification to the draft clinical report 150. As an example, the system may use a sentiment analysis technique with a portion of the transcript to determine an emotion associated with a statement by one of the speakers whose speech was captured and transcribed (e.g., happy, agitated, responsive, etc.). As a further example, the system may identify a characteristic of a portion of a transcript (e.g., linguistic prosody) that is mapped to a representation of the transcript (other than the text of the transcript itself). The system may also apply techniques such as sentiment analysis and semantic analysis to determine that one speaker has identified an emotional response or made another meta observation about the other speaker (e.g., Dr. Yu tells a patient, "You seem upset by this."). Meta observations may be used to infer data associated with transcribed text, in addition or instead of data that is explicitly stated in the transcribed text. Such meta observations may also be mapped to a representation of the portion of the transcript and incorporated into the draft clinical report 150.

The method 250 includes modifying the draft clinical report to include a representation of the mapped at least one portion of the generated transcript (256). As indicated above, the method 250 may modify the draft clinical report 150 to include text copied from the transcript into the report or to include a summary of a portion of the transcript generated by accessing a second mapping between a concept identified in the at least one portion of the transcript and a description of the concept, without including the text of the transcript; the modification may occur based upon the role of the speakers, upon an identification of the speakers, or based upon other data identified in the patient encounter context. The method 250 may include modifying the draft clinical report 150 based upon a preference associated with the first speaker (e.g., the physician). The method 250 may further include modifying the draft clinical report 150 to include a copy of the accessed transcript (e.g., in its entirety). The method 250 may further include storing, in a data structure, data representing an association between data stored in an electronic medical record about one of the first speaker and the second speaker identified as having a patient role and a portion of the transcript. A computing device executing a document generation system such as the system 100 that may determine whether to include transcribed data and, upon determining to include a representation of the data but not the data itself, executed functionality for generating new content based upon and representing dictation but not explicitly transcribed from the dictation and for inserting the generated content into a document results in an improved computing device providing non-conventional, non-generic functionality.

The method 250 includes providing the modified draft clinical report to a user (258). The method 250 may include providing the modified draft clinical report to a user such as the physician who spoke at the encounter. The method 250 may include providing the modified draft clinical report to a user such as a scribe, as described in further detail in connection with FIG. 3.

Figure 4:
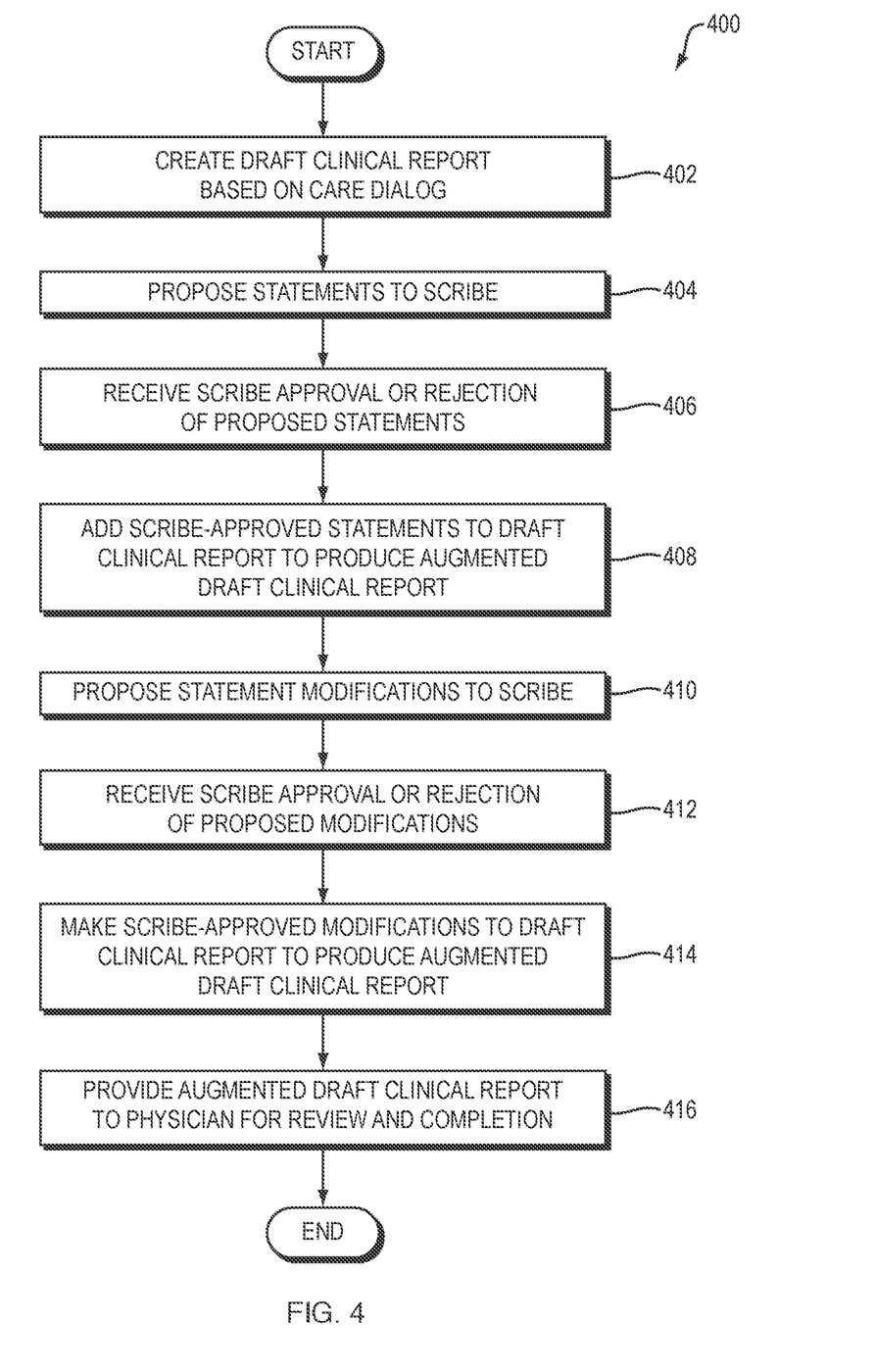
FIG. 4 is a flowchart of a method performed by the system of FIG. 3 according to one embodiment of the present invention.

Referring to FIG. 3, a dataflow diagram is shown of a system 300 for automatically generating an augmented draft clinical report 350 of an encounter between the physician 102a and a patient 102b according to one embodiment of the present invention. Referring to FIG. 4, a flowchart is shown of a method 400 performed by the system 300 of FIG. 3 according to one embodiment of the present invention.

The physician 102a and patient 102b may speak during the patient encounter in the ways described above in connection with FIGS. 1 and 2. The system 300 of FIG. 3 may create a draft transcript of the patient encounter in any of a variety of ways, including accessing a draft transcript generated by a separate system as indicated in connection with FIG. 2B.

Regarding the draft clinical report incorporating representations of data included in the transcript, and as shown in the example of FIG. 3, the system 300 uses the techniques of FIGS. 2A-B to produce the draft clinical report 150. The system 300 may, however, produce the draft clinical report 150 using techniques other than those disclosed herein in connection with FIGS. 2A-B. For example, the system 300 also includes a scribe 302 who, as described above, may be in the same room as the physician 102a and patient 102b, or who may be located remotely from the physician 102a and patient 102b, in which case the scribe 302 may listen to the care dialog over the Internet or other network. The draft clinical report 150 may be produced, in whole or in part, by the scribe 302. For example, the scribe 302 may type the draft clinical report 150 while listening to the (live or recorded) care dialog between the physician 102a and patient 102b. More generally, the method 200 of FIG. 2A may include both an automatic speech recognizer and the scribe 302, who may produce the draft clinical report 150 in combination with each other. For example, the automatic speech recognizer may produce draft statements within the draft clinical report 150, which the scribe 302 may edit within the draft clinical report 150.

The system 300 includes a statement generation module 304, which generates and proposes to the scribe 302, based on the draft clinical report 150, one or more statements 306 to be added to the draft clinical report 150 (FIG. 4, operation 404). The statement generation module 304 may receive a copy of the transcript with the draft clinical report 150. The statement generation module 304 may, for example, display the proposed statements 306 to the scribe 302 for review. The statement generation module 304 may generate the proposed statements 306 while the draft clinical report 150 is being generated (e.g., while the scribe 302 is typing the draft clinical report 150) and/or after the draft clinical report 150 has been generated.

The scribe 302 may provide, to the statement generation module 304, input 308 indicating approval or rejection of the proposed statements 306 (FIG. 4, operation 406). The statement generation module 304 adds any statements accepted by the scribe 302 to the draft clinical report 150, thereby producing the augmented draft clinical report 350 (FIG. 4, operation 408). The system 300 may then provide the augmented draft clinical report 350, rather than the draft clinical report 150, to the physician 102a for review and revision (FIG. 4, operation 416).

One advantage of the system 300 and method 400, therefore, is that they reduce the amount of time required to add statements to the draft clinical report 150, in comparison to prior art systems in which the human scribe 302 must type such statements manually into the draft clinical report. In contrast, in the system 300 and method 400, the scribe 302 merely needs to accept an automatically generated statement in order to add that statement to the draft clinical report, thereby saving the time required both to formulate and type such a statement. This is important not only because of the inherent benefit of increasing the speed with which the draft clinical report 150 may be updated, but also because, in the event that the scribe 302 is present during a live patient encounter between the physician 102a and the patient 102b, it may be difficult for the scribe 302 to keep up with the pace of the patient encounter if the scribe 302 is required to type all statements manually. If the scribe 302 cannot type quickly enough, important details of the patient encounter may be lost. The system 300 and method 400 therefore, may help to avoid omitting important details from the augmented draft clinical report 350 that is provided to the physician 102a for review.

As a human scribe works with a particular physician (e.g., the physician 102a) over time, the scribe may learn particular ways in which that physician prefers to express facts in their clinical reports, such as preferred word choices and levels of verbosity. Scribe turnover rates are high, with an average tenure of only 12-15 months. Each time a physician's scribe leaves and is replaced with a new scribe, the physician must again invest time to train the new scribe to comply with his or her preferred style of documentation.

The system 300 may address this problem in a variety of ways. For example, the statement generation module 304 may generate the proposed statements 306 to be written in the physician 102a's writing style. As another example, the system 300 may include a statement modification module 310, which may propose modifications 312 to existing statements in the draft clinical report 150 (such as statements that were written by the scribe), where such proposed modifications 312 would, if applied to the draft clinical report 150, make the draft clinical report 150 reflect the physician 102a's writing style more closely.

More specifically, the statement modification module 310 may generate and proposes, to the scribe 302, based on the draft clinical report 150, one or more modifications 312 to be made to existing statements in the draft clinical report 150 (FIG. 4, operation 410). The statement modification module 310 may, for example, display the proposed modifications 312 to the scribe 302 for review. The statement modification module 310 may generate the proposed modifications 312 while the draft clinical report 150 is being generated (e.g., while the scribe 302 is typing the draft clinical report 150) and/or after the draft clinical report 150 has been generated. The statement modification module 310 may analyze the transcript of the encounter as part of generating a proposed modification 312.

The scribe 302 may provide, to the statement modification module 310, input 314 indicating approval or rejection of the proposed modifications 312 (FIG. 4, operation 412). The statement modification module 310 makes any modifications accepted by the scribe 302 to the draft clinical report 150, thereby producing the augmented draft clinical report 350 (FIG. 4, operation 414). The system 300 may then provide the augmented draft clinical report 350, rather than the draft clinical report 150, to the physician 102a for review and revision (FIG. 4, operation 416).

The system 300 may propose statements 306 to add to the draft clinical report 150 and/or propose modifications 312 to the draft clinical report 150 based on, for example, any one or more of the following, in any combination:
  a priori context about the patient 102b (e.g., age or gender);
  the context of the draft clinical report 150 (e.g., which information has already been included in the draft clinical report 150 and which information is still missing); and
  the output of the signal processing module 114 and/or dialog mapping module 118, which map segments of the care dialog to likely clinical statements summarizing the contents of the care dialog.

Suggested edits to the draft clinical report 150 (e.g. the proposed statements 306 and the proposed modifications 312) may, for example, include: (1) proposed text to be added/modified in the draft clinical report 150; and (2) a location in the draft clinical report 150 where the edit is proposed to be made. Proposed text to be added or modified may include data to be added to one or more fields in a database (e.g., in an electronic medical record). Proposed text to be added or modified may include one or more additions or modifications to be made to a user interface element, such as adding a check to a check box or filling a radio button element. Proposed text to be added or modified may include text to be inserted into a document template. As will be understood by those of ordinary skill in the art, proposals may include proposals for modifications of any kind to any type of data.

Although the draft clinical report 150 and augmented draft clinical report 350 are shown as standalone documents, this is merely an example and not a limitation of the present invention. These documents 150 and 350 may, for example, be contained within an EMR system and/or clinical report editing tool. The scribe 302 and physician 102a may provide their respective inputs into such tools to edit the reports 150 and 350 within such tools.

Furthermore, although the descriptions of FIGS. 1-4 begin with the creation of the reports 150 and 350, in practice various steps may be performed before the techniques of FIGS. 1-4 are performed. For example, if the scribe 302 is to perform a live scribing service (i.e., if the scribe 302 is to create the reports 150 and 350 during the patient encounter), then the scribe 302 may prepare a chart for the patient 102b before the patient encounter and may brief the physician 102a, e.g., with the chart or a summary thereof, before the patient encounter beings. While the patient encounter is occurring, the scribe 302 may then listen to the care dialog and prepare the draft clinical report 150 and/or the augmented draft clinical report 350 using any of the techniques disclosed herein. The scribe 302 and/or system 300 may then provide the augmented draft clinical report 350 to the physician 102a for review, e.g., immediately after the patient encounter ends, or at a later time for the convenience of the physician 102a. The physician 102a may or may not communicate with the scribe 302 while reviewing, revising, and approving of the augmented draft clinical report 350. Such communication may be in person and/or remotely over a network connection.

If, instead, the scribe 302 creates the reports 150 and 350 after completion of the patient encounter (and possibly remotely from the physician 102a and patient 102b), then the physician 102a may initiate recording of the speech 104a-b, provide some or all of the encounter context data 112 (e.g., identity of the physician 102a and/or patient 102b), and stop recording of the speech 104a-b at the end of the patient encounter. The physician 102a may dictate additional information and/or instructions to the scribe 302 after the patient 102b leaves the room and before stopping recording of the speech 104a, in which case the physician speech 104a may include such additional information and/or instructions. The scribe 302 may then receive the audio output 108 and/or the automatically-generated draft clinical report 150. If the system 100 does not automatically generate the draft clinical report 150, then the scribe 302 may prepare the draft clinical report 150 manually, based on the audio output 108 and/or encounter context data 112. The scribe may then prepare the augmented draft clinical report 350 using the techniques disclosed herein, and provide the augmented draft clinical report 350 to the physician 102a for review as disclosed herein.

In FIG. 3, the statement generation module 304 and the statement modification module 310 may be integrated into a single module. Furthermore, these modules 304 and 310 may perform functions in addition to those disclosed above, such as any one or more of the following, in any combination: (1) template suggestion, (2) predictive typing, and (3) documentation alerts.

Template suggestion may, for example, include suggesting that a particular document template or sub-template be used for or within the draft clinical report 150. For example, if the physician 102a begins to discuss a finding, the system 300 may automatically identify and suggest inclusion of a template for that finding in the draft clinical report 150. Sub-templates for documentation of a procedure (e.g., an EKG) may be annotated with the procedure code (e.g., CPT code) identifying the procedure. If the natural language understanding system that processes the partially written report 150 detects an indication that a procedure is likely to be documented, or that the partial report 150 contains a (partial) free-form text documentation of a procedure for which a template would be available, then the system 300 may suggest the use of the respective template. Similarly, if the care dialog between the physician 102a and patient 102b contains an indication of a procedure, then the system 300 may suggest using the template associated with that procedure.

Predictive typing may, for example, include: (1) completing (or suggesting completion of) words and/or sentences in the draft clinical report 150 based on the textual context in the draft clinical report 150 and the outputs of the signal processing module 114 and dialog mapping module 118; and (2) suggesting alternative text snippet candidates (e.g., sentences and/or paragraphs) from which the scribe 302 can select for inclusion in the draft clinical report, where such suggestions may be made based on the textual context in the draft clinical report 150 and the outputs of the signal processing module 114 and dialog mapping module 118 (3) It may also include autocorrect and spell-checking functionality.

Conventional predictive typing may use statistical models of written and/or spoken language to predict the most likely word or word sequences, given a textual left and/or right context of the words to be predicted. Examples of such statistical models include n-gram language models and deep neural networks trained to model the statistical distribution of a training corpus (e.g., LSTMs). Such statistical models are typically built on large corpora of text or textual transcripts of spoken words taken from a target domain (e.g., medical reports). Such models may be refined with speaker dependent models that take the preferences and word choices of individual users or sub-populations into account. Such predictive models may be used to suggest word or sentence completions in a text editor. Their use, however, is limited by the number of word choices that are likely in a given context. In particular, it is usually not possible to use such models to predict sentence completions of more than one or two words, given the high entropy of the probability distribution of natural language.

Embodiments of the present invention address this limitation of conventional predictive typing by modeling the distribution of medical language conditioned on a representation of the care dialog between the patient 102b and the physician 102a. In particular, rather than modeling the likelihood of a word W_n given a word context (typically the preceding words W_n−1, . . . , W_1) and domain D as P(W_n|W_n−1, . . . , W_1, D), embodiments of the present invention model the same conditioned additionally on a representation of the output of the care dialog (e.g., the state of the draft clinical report 150 and/or augmented draft clinical report 350) at any given point in time C(t) as P(W_n|W_n−1, . . . , W_1, D, C(t)).

The representation C(t) may contain, for example, a transcript of the words spoken by the physician 102a and patient 102b in the care dialog and a partial coding of such words to indicate procedures, findings, and measurements (e.g., temperature measurements if spoken by the physician 102a). The system 100 may access data associated with the patient 102b and stored in any system or subsystem accessible by the system 100 to inform the predictive typing model. As one example, the system 100 may access data associated with the patient 102b and stored in an electronic medical record (such as a list of medications associated with the patient 102b).

One way in which such a model may be implemented is as follows:

$$P(W\_n|W\_n-1, \ldots, W\_1, D, C(t)) = \sim P(W\_n| W\_n-1, \ldots, W\_1, D, P) * P(P|C(t))$$

where P represents a relatively course-grained classification of typical encounters, e.g., the type of surgical procedure performed, a type of visit or a purely data-driven classification of report types into a small number of classes for which we can independently estimate P(W_n|W_n−1, W_1, D, P) using known language modelling methods. P(P|C(t)) may be implemented using well-known data classificators, e.g., SVMs or deep neural networks.

As for regular language models, the new statistical models described above may be made user-dependent by adaptation on the target user's (e.g., physician 102a's) target data. The resulting models may then be used for any one or more of the following, in any combination:

Predictive typing.

Providing alternatives for full sentences likely to be added to the draft clinical report 150 at the current cursor position, or at any position in the document based on information present in the care dialog, but not yet reflected in the current draft clinical report 150.

Providing suggestions to re-formulate sentences and/or paragraphs contained in the draft in a way that is more consistent with the physician 102a's documentation habits.

Documentation alerts may include displaying visible alerts notifying the scribe 302 of documentation guidelines and best practices, information that is missing and/or inconsistent in the draft clinical report 150, and reminders, or, generally, of a portion of the draft clinical report that requires additional modification. For example, if the scribe 302 is documenting an EKG procedure, the system 300 may remind the scribe 302 that the documentation for an EKG procedure must minimally contain information on at least any three of the following six elements: (1) the rhythm or rate; (2) axis; (3) intervals; (4) segments; (5) notation of a comparison with a prior EKG if one was available to the physician 102a; and (6) a summary of the patient 102b's clinical condition. The system 300 may track the progress of the draft clinical report 150 and remove such a reminder when the system 300 determines that the draft clinical report 150 satisfies the minimum requirements. The system 300 may display such alerts to the scribe 302, and may display a subset of those alerts (e.g., any alerts that the scribe 302 could not resolve and that are relevant to the physician 102a) to the physician 102a when the augmented draft clinical report 350 is displayed to the physician 102a. As a further example of such alerts, the system 300 may display individual reminders or a plurality of reminders, including, for example, a plurality of reminders that form a "to-do" list.

For example, M*Modal's Computer Assisted Physician Documentation (CAPD) infrastructure provides the capability to interpret the content of a clinical note (e.g., the draft clinical report 150 and the augmented draft clinical report 350) incrementally, while it is written, in light of encounter context data 112. M*Modal CDI Engage is a product that assists physicians by raising alerts based on this CAPD infrastructure. Embodiments of the present invention may incorporate CAPD and/or CDI Engage to perform functions disclosed herein. For example, functionality provided by the CAPD infrastructure may be used to alert a physician or scribe about various aspects related to clinical documentation, including creating reminders and automatically removing reminders once the draft clinical report 150 addresses a modification or requirement specified by the reminder.

Furthermore, embodiments of the present invention may expand on CAPD and/or CDI Engage to perform any one or more of the following functions, in any combination:

(1) Provide tiered feedback to the scribe 302 in the form of alerts while the scribe 302 is generating the clinical reports 150 and 350. The scribe 302 has the option to accept/resolve the alert, to suppress it, or to escalate it to be seen by the physician 102a immediately or at a later time.

(2) Take the non-transcribed care dialog (C(t), above) into account to, for example, generate an alert on important content present in C(t) that is not yet reflected in the draft reports 150 and 350 authored by the scribe 302.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more computers, computer processors, and/or other elements of a computer system. Such features are either impossible or impractical to implement mentally and/or manually. For example, the system 100 and method 200 use a signal processing module 114 to separate the physician speech 116a and the patient speech 116b from each other in the audio output 108.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

What is claimed is:

1. A method for automatically modifying, by a computer-automated tool, a draft clinical report to incorporate representations of data generated based on data extracted from captured speech, the method comprising:
   accessing, by a dialog mapping module executed by a computing device, a transcript of an encounter between a patient and a healthcare professional, the transcript including (i) an identification of a role of a first speaker at a portion of the transcript including a transcription of captured speech of the first speaker and (ii) an identification of a role of a second speaker at a portion of the transcript including a transcription of captured speech of the second speaker;
   mapping, by the dialog mapping module, at least one portion of the transcript of captured speech to a portion of a draft clinical report related to the encounter, based on the role of at least one of the first speaker and the second speaker;
   modifying, by the dialog mapping module, based on an encounter context data, the draft clinical report to include a representation of the mapped at least one portion of the generated transcript, the representation including a proposed statement written in a linguistic writing style of the healthcare professional, wherein modifying the draft clinical report to include the representation further comprises:
      accessing a second mapping between a concept identified in the portion of the transcript and a description of the concept;
      generating a summary of the portion of the transcript;
      including the summary in the proposed statement without including the text of the portion of the transcript; and
   providing, by the dialog mapping module, the modified draft clinical report to a user.

2. The method of claim 1, wherein modifying the draft clinical report to include the representation further comprises modifying the draft clinical report to include text copied from a portion of the transcript into the report.

3. The method of claim 1 further comprising receiving an identification of the first speaker.

4. The method of claim 3, wherein modifying further comprises modifying the draft clinical report to include text selected based upon a preference associated with the identified first speaker.

5. The method of claim 3, wherein modifying further comprises determining a level of detail to include from the transcript in the portion of the draft clinical report, based upon a preference associated with the identified first speaker.

6. The method of claim 1, wherein modifying the draft clinical report further comprises including a copy of the accessed transcript.

7. The method of claim 1 further comprising storing, in a data structure, data representing an association between data stored in an electronic medical record about one of the first speaker and the second speaker identified as having a patient role and a portion of the transcript.

8. The method of claim 1 further comprising:
   generating a proposed modification to the draft clinical report;
   receiving input accepting the proposed modification; and
   modifying the draft clinical report to include the proposed modification.

9. The method of claim 1 further comprising displaying a visible alert notifying the user of a portion of the draft clinical report that requires additional modification.

10. The method of claim 9 further comprising:
    determining that the portion of the draft clinical report no longer requires additional modification; and
    automatically removing the visible alert based upon the determination.

11. A non-transitory computer-readable medium storing computer program instructions executable by at least one computer processor to perform a method for automatically modifying, by a computer-automated tool, a draft clinical report to incorporate representations of data generated based on data extracted from captured speech, the method comprising:
    accessing, by a dialog mapping module executed by a computing device, a transcript of an encounter between a patient and a healthcare professional, the transcript including (i) an identification of a role of a first speaker at a portion of the transcript including a transcription of captured speech of the first speaker and (ii) an identification of a role of a second speaker at a portion of the transcript including a transcription of captured speech of the second speaker;
    mapping, by the dialog mapping module, at least one portion of the transcript of captured speech to a portion of a draft clinical report related to the encounter, based on the role of at least one of the first speaker and the second speaker;
    modifying, by the dialog mapping module, based on an encounter context data, the draft clinical report to include a representation of the mapped at least one portion of the generated transcript, the representation including a proposed statement written in a linguistic writing style of the healthcare professional, wherein modifying the draft clinical report to include the representation further comprises including a summary of the portion of the transcript generated by accessing a second mapping between a concept identified in the portion of the transcript and a description of the concept, without including the text of the portion of the transcript; and providing the modified draft clinical report to a user.

12. The non-transitory computer-readable medium of claim 11 further comprising instructions to modify the draft clinical report to include text copied from a portion of the transcript into the report.

13. The non-transitory computer-readable medium of claim 11 further comprising instructions to receive an identification of the first speaker.

14. The non-transitory computer-readable medium of claim 13 further comprising instructions to modify the draft clinical report to include text selected based upon a preference associated with the identified first speaker.

15. The non-transitory computer-readable medium of claim 13 further comprising instructions to determine a level of detail to include from the transcript in the portion of the draft clinical report, based upon a preference associated with the identified first speaker.

16. The non-transitory computer-readable medium of claim 11 further comprising instructions to include a copy of the accessed transcript.

17. The non-transitory computer-readable medium of claim 11 further comprising instructions to store, in a data structure, data representing an association between data stored in an electronic medical record about one of the first speaker and the second speaker identified as having a patient role and a portion of the transcript.

18. The non-transitory computer-readable medium of claim 11 further comprising instructions to:

generate a proposed modification to the draft clinical report;

receive input accepting the proposed modification; and modify the draft clinical report to include the proposed modification.

19. The method of claim 1, wherein the proposed statement is written using a preferred word choice of the healthcare professional.

20. The non-transitory computer-readable medium of claim 11, wherein the proposed statement is written using a preferred word choice of the healthcare professional.

* * * * *

UNITED STATES PATENT AND TRADEMARK OFFICE
CERTIFICATE OF CORRECTION

PATENT NO. : 11,158,411 B2
APPLICATION NO. : 15/897945
DATED : October 26, 2021
INVENTOR(S) : Koll et al.

Page 1 of 1

It is certified that error appears in the above-identified patent and that said Letters Patent is hereby corrected as shown below:

In the Claims

Column 18
Line 9, In Claim 2, delete "a portion" and insert -- the portion --, therefor.
Line 19, In Claim 5, delete "a preference" and insert -- the preference --, therefor.
Line 27, In Claim 7, delete "a portion" and insert -- the portion --, therefor.
Line 35, In Claim 9, delete "a portion" and insert -- the portion --, therefor.

Column 19
Line 12, In Claim 12, before "text", insert -- the --.
Line 12, In Claim 12, delete "a portion" and insert -- the portion --, therefor.
Line 18, In Claim 14, before "text", insert -- the --.
Line 23, In Claim 15, delete "a preference" and insert -- the preference --, therefor.

Column 20
Line 9, In Claim 17, delete "a portion" and insert -- the portion --, therefor.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*